United States Patent
Fuhr et al.

(10) Patent No.: US 11,085,834 B2
(45) Date of Patent: Aug. 10, 2021

(54) DEVICE AND METHOD FOR MONITORING THE TEMPERATURE OF A CRYOGENICALLY PRESERVED BIOLOGICAL SAMPLE

(71) Applicant: Fraunhofer-Gesellschaft zur Foerderung der angewandten Forschung e. V., Munich (DE)

(72) Inventors: Guenter R. Fuhr, Berlin (DE); Heiko Zimmermann, Waldbrunn (DE)

(73) Assignee: Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 471 days.

(21) Appl. No.: 16/097,259

(22) PCT Filed: Mar. 31, 2017

(86) PCT No.: PCT/EP2017/000402
§ 371 (c)(1),
(2) Date: Oct. 28, 2018

(87) PCT Pub. No.: WO2017/186329
PCT Pub. Date: Nov. 2, 2017

(65) Prior Publication Data
US 2019/0113397 A1    Apr. 18, 2019

(30) Foreign Application Priority Data
Apr. 27, 2016    (DE) .......................... 102016005078.0

(51) Int. Cl.
*G01K 11/02*    (2006.01)
*G01K 13/00*    (2021.01)
(Continued)

(52) U.S. Cl.
CPC ......... *G01K 13/006* (2013.01); *A01N 1/0221* (2013.01); *A01N 1/0236* (2013.01);
(Continued)

(58) Field of Classification Search
CPC ........ G01K 11/06; G01K 1/02; G01K 13/006; G01K 11/02; C08F 2500/12;
(Continued)

(56) References Cited

U.S. PATENT DOCUMENTS

| | | |
|---|---|---|
| 1,917,048 A | 7/1933 | Midgley, Jr. |
| 2,955,942 A | 10/1960 | Fenity et al. |

(Continued)

FOREIGN PATENT DOCUMENTS

| | | |
|---|---|---|
| CN | 1419512 A | 5/2003 |
| CN | 1687757 A | 10/2005 |

(Continued)

OTHER PUBLICATIONS

English Abstract for CN 1687757 A (2005).
(Continued)

*Primary Examiner* — Gail Kaplan Verbitsky
(74) *Attorney, Agent, or Firm* — Caesar Rivise, PC (57) ABSTRACT

The invention relates to a device for monitoring the temperature of a cryogenically preserved biological sample. The device (10) comprises a sample container (1) having a receptacle space (2) for accommodating a biological sample (6). The device further comprises at least one chamber (11), the interior (12) of which is not fluidically connected to the receptacle space, and which is at least partially filled with an indicator substance (7) having a boiling point or sublimation temperature in a range from −10° C. to −140° C. The chamber (11) further has at least one opening via which the indicator substance (7) can escape from the interior (12) of the chamber (11) upon exceeding its boiling point or subli-
(Continued)

mation point. The invention further relates to a method for monitoring the temperature of a cryogenically preserved biological sample.

15 Claims, 3 Drawing Sheets

(51) Int. Cl.
| | |
|---|---|
| *A01N 1/02* | (2006.01) |
| *C12M 1/00* | (2006.01) |
| *C12M 1/24* | (2006.01) |
| *C12M 3/00* | (2006.01) |
| *C12N 5/0735* | (2010.01) |
| *G01K 11/06* | (2006.01) |
| *G01K 11/12* | (2021.01) |

(52) U.S. Cl.
CPC ........... *A01N 1/0268* (2013.01); *C12M 1/007* (2013.01); *C12M 1/24* (2013.01); *C12M 23/08* (2013.01); *C12M 23/42* (2013.01); *C12N 5/0606* (2013.01); *G01K 11/02* (2013.01); *G01K 11/06* (2013.01); *G01K 11/12* (2013.01); *C12M 23/14* (2013.01); *G01K 2203/00* (2013.01)

(58) Field of Classification Search
CPC .. G01N 31/229; G01N 21/05; G01N 33/5302; G01N 1/42; G01N 31/22; G01N 33/1886; G01N 33/1893; G01N 33/48
USPC ............ 374/45, 16, 100.101, 105, 102, 160; 116/216, 217
See application file for complete search history.

(56) References Cited

U.S. PATENT DOCUMENTS

| | | | |
|---|---|---|---|
| RE25,499 E | 12/1963 | Fenity et al. | |
| 3,701,282 A | 10/1972 | Peterson | |
| 3,958,528 A * | 5/1976 | Hill ........................ | G01K 11/06 116/219 |
| 4,134,359 A | 1/1979 | Redpath | |
| 4,137,049 A | 1/1979 | Couch et al. | |
| 4,195,056 A | 3/1980 | Patel | |
| 4,280,361 A | 7/1981 | Sala | |
| 4,509,449 A | 4/1985 | Chalmers | |
| 4,664,056 A | 5/1987 | Jehanno | |
| 4,844,622 A | 7/1989 | Weiss | |
| 5,057,434 A | 10/1991 | Prusik et al. | |
| 5,102,233 A | 4/1992 | Staerk et al. | |
| 5,182,212 A | 1/1993 | Jalinski | |
| 5,282,684 A | 2/1994 | Holzer | |
| 7,097,353 B2 | 8/2006 | Wieder | |
| 7,387,438 B2 | 6/2008 | Parker | |
| 7,415,939 B2 * | 8/2008 | Dip ........................ | G01K 11/06 116/216 |
| 8,122,844 B2 | 2/2012 | Smith et al. | |
| 8,168,138 B2 | 5/2012 | Che et al. | |
| 8,173,388 B2 | 5/2012 | Pasmore et al. | |
| 9,046,292 B2 | 6/2015 | Burke et al. | |
| 9,097,594 B2 | 8/2015 | Rastegar et al. | |
| 9,222,903 B2 | 12/2015 | Crevatin et al. | |
| 9,279,732 B2 | 3/2016 | Parker | |
| 9,464,973 B2 | 10/2016 | Fuhr et al. | |
| 9,618,398 B2 | 4/2017 | Deng et al. | |
| 10,048,138 B2 | 8/2018 | Smith et al. | |
| 10,408,686 B2 | 9/2019 | Newport et al. | |
| 2003/0047477 A1 | 3/2003 | Nygardh et al. | |
| 2006/0078036 A1 | 4/2006 | Wieder | |
| 2007/0098039 A1 | 5/2007 | Parker | |
| 2008/0056329 A1 | 3/2008 | Smith et al. | |
| 2009/0129434 A1 | 5/2009 | Creus et al. | |
| 2014/0318437 A1 | 10/2014 | Hong et al. | |
| 2014/0334520 A1 | 11/2014 | Chen et al. | |
| 2019/0113397 A1 | 4/2019 | Fuhr et al. | |
| 2020/0029551 A1* | 1/2020 | Fuhr ................... | A01N 1/0236 |
| 2020/0362292 A1* | 11/2020 | Hoehse ................. | G01N 21/31 |
| 2021/0010873 A1* | 1/2021 | Aida .................... | G01N 31/229 |

FOREIGN PATENT DOCUMENTS

| | | |
|---|---|---|
| CN | 1809734 A | 7/2006 |
| CN | 101198850 A | 6/2008 |
| CN | 201731955 U | 2/2011 |
| CN | 102369387 A | 3/2012 |
| CN | 102379278 A | 3/2012 |
| CN | 102844649 A | 12/2012 |
| CN | 102853946 A | 1/2013 |
| CN | 104501994 A | 4/2015 |
| CN | 104583741 A | 4/2015 |
| CN | 103630503 B | 4/2016 |
| CN | 205175785 U | 4/2016 |
| CN | 109152354 A | 1/2019 |
| DE | 74651 A1 | 7/1970 |
| DE | 2130926 A | 12/1972 |
| DE | 2504078 A1 | 8/1976 |
| DE | 8435794 U1 | 3/1985 |
| DE | 3712201 A1 | 9/1988 |
| DE | 3716972 A1 | 12/1988 |
| DE | 3731268 A1 | 4/1989 |
| DE | 3838661 A1 | 6/1989 |
| DE | 19960920 A1 | 6/2001 |
| DE | 20301688 U1 | 5/2003 |
| DE | 10203630 A1 | 8/2003 |
| DE | 20301123 U1 | 3/2004 |
| DE | 102005041495 A1 | 3/2007 |
| DE | 102006003995 A1 | 8/2007 |
| DE | 102006003995 B4 | 4/2008 |
| DE | 102006045821 A1 | 4/2008 |
| DE | 102008028334 A1 | 12/2009 |
| DE | 102008031666 A1 | 1/2010 |
| DE | 102008031666 B4 | 5/2010 |
| DE | 102006055331 B4 | 12/2010 |
| DE | 102010052434 A1 | 5/2012 |
| DE | 102011010120 A1 | 8/2012 |
| DE | 102011115467 A1 | 4/2013 |
| DE | 102012202565 A1 | 8/2013 |
| DE | 102013108557 B3 | 11/2014 |
| DE | 102014018308 A1 | 6/2016 |
| EP | 0606033 A1 | 7/1994 |
| EP | 1560009 A1 | 8/2005 |
| EP | 2937850 A1 | 10/2015 |
| EP | 2984928 A1 | 2/2016 |
| FR | 2370269 A2 | 6/1978 |
| FR | 2508164 A1 | 12/1982 |
| FR | 2641611 A1 | 7/1990 |
| FR | 2662798 A1 | 12/1991 |
| FR | 2929705 A1 | 10/2009 |
| FR | 3013836 A1 | 5/2015 |
| GB | 2416842 A | 2/2006 |
| JP | 55-500 A | 1/1980 |
| JP | 56-1322 A | 1/1981 |
| JP | S6055235 A | 3/1985 |
| JP | 60-500460 A | 4/1985 |
| JP | 4-109336 U | 9/1992 |
| JP | H05-99754 A | 4/1993 |
| JP | H07-167716 A | 7/1995 |
| JP | 2002-323386 A | 11/2002 |
| JP | 2004-77215 A | 3/2004 |
| JP | 2006047030 A | 2/2006 |
| JP | 2008151716 A | 7/2008 |
| JP | 2008542736 A | 11/2008 |
| JP | 2009-128137 A | 6/2009 |
| JP | 2009-524806 A | 7/2009 |
| JP | 2012-173282 A | 9/2012 |
| JP | 2012219017 A | 11/2012 |
| WO | 9802722 A1 | 1/1998 |
| WO | 0047964 A1 | 8/2000 |
| WO | 2004077001 A1 | 9/2004 |
| WO | 2006128899 A1 | 12/2006 |
| WO | 2007012132 A1 | 2/2007 |
| WO | 2007039094 A1 | 4/2007 |

(56) References Cited

FOREIGN PATENT DOCUMENTS

| WO | 2007085385 A1 | 8/2007 |
|---|---|---|
| WO | 2008027814 A2 | 3/2008 |
| WO | 2015078767 A1 | 6/2015 |

OTHER PUBLICATIONS

English Abstract for CN 201731955 U (2011).
English Abstract for CN 104501994 A (2015).
English Abstract for JP 2002-323386 A (2002).
English Abstract for JP 2004-77215 A (2004).
English Abstract for JP 2009-128137 A (2009).
English Abstract for JP 2012-173282 A (2012).
Chinese Office Action with Translation dated Dec. 17, 2020.
Pitt et al. (2008). 2008 Best practices for repositories: collection, storage, retrieval and distribution of biological materials for research. Cell Preservation Technology, 6(1), 3-58.
Ren et al. (2009). Evaluation of an outside-the-cold-chain vaccine delivery strategy in remote regions of western china. Public Health Reports, 124, 745-750.
Ruedel et al. (2015). Richtlinie zur probenahme and probenbearbeitung: transport von umweltproben unter cryobedingungen. Umwelt Bundesamt, 1-8.
Shirley et al. (2009). A large-scale cryoelectronic system for biological sample banking. Cryogenics, 49, 638-642.
Simione. (2012). A guide for proper cryogenic preservation. Thermo Fisher Scientific, 1-14.
Thermo Fisher Scientific. (2010). Thermo scientific nunc cryobank vials and bank-it tube system. Product Literature, 1-8.
Thermo Fisher Scientific. (2014). Automated sample storage resource guide. Product Literature, 1-24.
Thermo Fisher Scientific. (2015). Thermo scientific sample storage products. Product Literature, 1-18.
Thermo Fisher Scientific. (2016). The anatomy of the a cryogenic tube. Product Literature, 1-8.
WarmMark. (2014). WarmMark Technical Data Sheet. Product Literature, 1-11.
International Search Report of PCT/EP2017/000402 (dated Jul. 7, 2017).
English Abstract for CN 103630503 B (2016).
English Abstract for CN 205175785 U (2016).
Machine Translation for DD 74651 A1 (1970).
English Abstract for DE 2130926 A (1972).
English Abstract for DE 2504078 A1 (1976).
English Abstract for DE 3712201 A1 (1988).
English Abstract for DE 3716972 A1 (1988).
English Abstract for DE 3731268 A1 (1989).
English Abstract for DE 3838661 A1 (1989).
Machine Translation for DE 8435794 U1 (1985).
English Abstract for DE 10203630 A1 (2003).
English Abstract for DE 19960920 A1 (2001).
English Abstract for DE 20301123 U1 (2004).
English Abstract for DE 20301688 U1 (2003).
English Abstract for DE 102005041495 A1 (2007).
English Abstract for DE 102006045821 A1 (2008).
English Abstract for DE 102008028334 A1 (2009).
English Abstract for DE 102008031666 A1 (2010).
English Abstract for DE 102008031666 B4 (2010).
English Abstract for DE 102010052434 A1 (2012).
English Abstract for DE 102011010120 A1 (2012).
English Abstract for DE 102011115467 A1 (2013).
English Abstract for DE 102012202565 A1 (2013).
English Abstract for DE 102013108557 B3 (2014).
English Abstract for DE 102014018308 A1 (2016).
English Abstract for FR 2370269 A2 (1978).
English Abstract for FR 2508164 A1 (1982).
English Abstract for FR 2641611 A1 (1990).
English Abstract for FR 2662798 A1 (1991).
English Abstract for FR 2929705 A1 (2009).
English Abstract for FR 3013836 A1 (2015).
English Abstract for JP S6055235 A (1985).
Machine Translation for JP 2006047030 A (2006).
Machine Translation for JP 2008151716 A (2008).
3M (2006). 3M Monitor Mark. Time Temperature Indicators. Product Literature,1-4.
Biocision LLC. (2013). Snap freezing using dry ice or liquid nitrogen. Product Literature, 1-2.
Capture of http://www.cryoguard.com/key-information/ retrieved from internet archive on Jun. 21, 2017.
Durst et al. (2007). Management, interchange and reproducible execution of sample preparation knowledge in collaborative research scenarios. Proceedings of I-Know '07 Graz, Austria. 111-117.
FreezCube (2008). Screenshot from video at 2:23. FreezCube, Invention Géniale! Youtube. Published at https://www.youtube.com/watch?v=ZjPf7YP5r68 on Sep. 22, 2008.
FreezCube (2010). Le gardien de vos surgelees. Product Literature, 1-13.
Germann et al. (2013). Temperature fluctuations during deep temperature cryopreservation reduce PBMC recovery, viability and T-cell function. Cryobiology, 67, 193-200.
Goodell et al. (2016). Ring test evaluation of the detection of influenza A virus in swine oral fluids by real-time reverse-transcription polymerase chain reaction and virus isolation. The Canadian Journal of Veterinary Research, 80, 12-20.
Ihmig et al. (2006). Cryogenic electronic memory infrastructure for physically related "continuity of care records" of frozen cells. Cryogenics, 46, 312-320.
Ihmig et al. (2009). The technology of the global HIV vaccine research cryorepository. Engineering in Life Sciences, 9 (5), 376-383.
Ihmig et al. GHRC/CAVD-technology: new identification, storage and distribution technologies for vaccine related reagents and specimens, In AIDS Research and Human Retroviruses (M. Liebert ed. 2010). A68-A69.
Ihmig et al. (2013). Frozen cells and bits: cryoelectronics advances biopreservation. IEEE Pulse, 4(5), 35-43.
Meiser et al. (2009). Entwicklung and evaluierung einer mikrosystem-basierten anlage zur kryokonservierung von multizellulaeren aggregaten. Proceedings of Mirosystemtechnik Kongress, Berlin, Germany, Paper 102.
National Institute of Environmental Health Sciences. (2015). Specimen cold chain SOP—processing, transportation & storage temperatures. Product Literature, 1-6.
Partial Translation for FreezCube (2010). Le gardien de vos surgelees. Product Literature, 1-13.
Partial Translation for Pretschner. (2011). Thermotransportsysteme fuer biomedizische anwendungen. Proceedings of Innovationsforum Bio-Logistik, Leipzig, Germany. Powerpoint Presentation, 75-88.
CN 103630503 B, English Abstract.
CN 205175785 U, English Abstract.
DD 74651 A1, Machine Translation.
DE 2130926 A, English Abstract.
DE 2504078 A1, English Abstract.
DE 3712201 A1, English Abstract.
DE 3716972 A1, English Abstract.
DE 3731268 A1, English Abstract.
DE 3838661 A1, English Abstract.
DE 8435794 U1, Machine Translation.
DE 10203630 A1, English Abstract.
DE 19960920 A1, English Abstract.
DE 20301123 U1, English Abstract.
DE 20301688 U1, English Abstract.
DE 102005041495 A1, English Abstract.
DE 102006003995 A1, WO 2007085385 English Abstract (p. 1).
DE 102006045821 A1, English Abstract.
DE 102006055331 B4, WO 2007085385 English Abstract (p. 1).
DE 102008028334 A1, English Abstract.
DE 102008031666 A1, English Abstract.
DE 102008031666 B4, English Abstract.
DE 102010052434 A1, English Abstract.
DE 102011010120 A1, English Abstract.
DE 102011115467 A1, English Abstract.
DE 102012202565 A1, English Abstract.

(56) References Cited

OTHER PUBLICATIONS

DE 102013108557 B3, English Abstract.
DE 102014018308 A1, English Abstract.
FR 2370269 A2, English Abstract.
FR 2508164 A1, English Abstract.
FR 2641611 A1, English Abstract.
FR 2662798 A1, English Abstract.
FR 2929705 A1, English Abstract.
FR 3013836 A1, English Abstract.
JP S6055235 A, English Abstract.
JP 2006047030 A, Machine Translation.
JP 2008151716 A, Machine Translation
WO 2006128899 A1, English Abstract on p. 1
WO 2007085385 A1, English Abstract on p. 1
WO 2015078767, English Abstract on p. 1.
FreezCube (2010). Le gardien de vos surgeles, Product Literature, 1-13, Partial Translation.
Meiser et al. (2009) Entwicklung und evaluierung einer mikrosystem-basierten anlage zur kryokonservierung von multizellulaeren aggregaten. Proceedings of Mirosystemtechnik Kongress, Berlin, Germany, Paper 102, English Abstract on p. 1.
Pretschner. (2011), Thermotransportsysteme fuer biomedizische anwendungen. Proceedings of Innovationsforum Bio-Logistik, Leipzig, Germany. PowerPoint Presentation, 75-88, Partial Translation—Slides 9, 10, 11, 12, 13, and 14.
Ruedel et al. (2015). Richtlinie zur probenahme und probenbearbeitung: transport von umweltproben unter cryobedingungen. Umwelt Bundesamt, 1-8, Machine Translation pages 4-8.
U.S. Appl. No. 16/095,549, filed Oct. 22, 2018.
U.S. Appl. No. 16/095,591, filed Oct. 22, 2018.
U.S. Appl. No. 16/095,936, filed Oct. 23, 2018.
U.S. Appl. No. 16/097,111, filed Oct. 26, 2018.
U.S. Appl. No. 16/097,255, filed Oct. 27, 2018.
English Abstract for EP 0606033 A1 (1994).
Machine Translation of Abstract for JP 4-109336 U (1992).
English Abstract for JP H07-167716 A (1995).
English Abstract for JP 2012219017 A (2012).

* cited by examiner

DEVICE AND METHOD FOR MONITORING THE TEMPERATURE OF A CRYOGENICALLY PRESERVED BIOLOGICAL SAMPLE

CROSS-REFERENCE TO RELATED APPLICATIONS

This application is a U.S. National Phase Application of PCT/EP2017/000402, filed Mar. 31, 2017, which claims priority to DE 10 2016 005 078.0, filed Apr. 27, 2016, the contents of which applications are incorporated herein by reference in their entireties for all purposes.

BACKGROUND OF THE INVENTION

The invention relates to a device for temperature monitoring of a cryopreserved biological sample. The invention further relates to a method for temperature monitoring of a cryopreserved biological sample.

The low-temperature preservation (cryopreservation) of cells is hitherto the only possibility of stopping vital processes reversibly (maintaining vitality) at a cellular level such that they can restart after heating to physiological temperatures. Cryopreservation has developed by way of large biobanks in recent decades to become an essential element for clinics, pharmaceutical companies, species survival, environmental protection and health provision. Biological material is stored in low-temperature-compatible sample containers (cryogenic containers), e.g. tubes, straws and bags, of various sizes. In the case of cryopreservation, the stored biomaterial is frozen while maintaining the vitality of the sample material, usually at temperatures below $-80°$ C., for living collections below $-140°$ C. to the temperature of liquid nitrogen. The term "cryogenic sample" is also used below for a cryopreserved sample or a sample intended for cryopreservation.

Numerous techniques have been developed for macroscopic samples, such as e.g. blood or tissue, for sample storage at low temperatures. There is a tendency in modern medicine, genetic engineering and biology to increasingly subject small samples to cryopreservation. For example, small suspension volumes (milliliter or below) with suspended cells or groups of cells are frozen. The cryopreservation of cells from in-vitro cultures is primarily carried out in a suspension. However, the majority of biomedically significant cells require a substrate contact for their propagation and proper development. Samples are therefore frozen in the substrate-bound state possibly after cultivation.

The quality of the samples is of decisive importance since they are used for cell therapies in clinics, the development of pharmaceuticals and biotechnological products, as national resources and many other things. The storage time varies from a few days up to decades, with a tendency towards long-term storage. The samples are stored in cooled containers, are usually located in metal drawers and racks, with which they are subjected to temperature fluctuations in the case of new deposits or removals. In the case of living storage (cells, cell suspensions and pieces of tissue), it is not only the uninterrupted cooling chain which plays a vital role, but also the avoidance of large jumps in temperature in the deep-freezing phase. Since it is not unknown during removal for cryogenic containers to heat up to temperatures of $-80°$ C. to $-20°$ C., despite the fact they are still frozen, reductions in quality unknowingly arise which not only reduce the value of the sample, but can also lead to life-threatening situations when they are used in the clinical sector. Even if samples have only thawed briefly, it is not possible to see in the refrozen state that they no longer match the original condition. However, it is especially important to not only identify a thawing of the biomaterial, but also to document the exceeding of a threshold temperature in the range between $-140°$ C. and $-20°$ C. Temperature control and documentation for each sample is the requirement, one which has hitherto only seldom been satisfied, and if so, with high technical outlay. One must also remember extensive laboratory tests after thawing which also use valuable sample material and generate costs even in the case of cryogenic samples which have become worthless in the interim.

One object of the invention is thus to provide a device for temperature monitoring of a cryopreserved biological sample, with which disadvantages of conventional techniques can be avoided. A further object is to provide an improved method for temperature monitoring of a cryopreserved biological sample with which disadvantages of conventional techniques can be avoided and which is characterized by a simplified execution of the method.

A further object is to provide a possibility in order to be able to identify from as simple as possible a marker whether a cryogenic sample has been heated above a definable threshold temperature, even if only for a short time. It must be possible to fix the threshold temperature in the range between $-20°$ C. and $140°$ C. prior to freezing. This should be possible quickly and in a readily apparent manner at each individual cryogenic sample and at thus millions of samples, must not change the biomaterials and should already be carried out in the deep-frozen state. If possible it should be possible to detect the condition of the sample even in the storage container since every time the sample is removed from and returned to storage there is the risk of a change in sample of a plurality of samples in the store since entire racks are generally pulled up. The device and the method should be easy to handle, low-temperature-tolerant and adjustable. It must consume no or only a small amount of energy and result in only the smallest of costs since the storage of a biological sample in the cooled state should only cost a few Euros in terms of total outlay. The materials used must also satisfy this requirement. It would furthermore be desirable if not only the exceeding of a threshold temperature to be monitored, but also a measure of the period of time of this exceeding could be detected.

These objects are achieved by devices and methods of the invention and are explained in greater detail in the following description with partial reference to the figures.

SUMMARY OF THE INVENTION

According to a first aspect of the invention, the stated objects are achieved by a device for temperature monitoring of a cryopreserved biological sample. The device comprises a sample container with a receiving space (sample reservoir) for receiving a biological sample. The sample container is in particular a cryogenic sample container. The receiving cavity may contain a cryopreserved sample.

The device further comprises a chamber, the inner space of which is not fluidically connected to the receiving space and is filled at least partially with an indicator substance, the boiling temperature or sublimation temperature of which lies in a range from $-10°$ C. to $-140°$ C. The boiling temperature may be the normal boiling temperature, i.e. the boiling temperature at normal pressure (1013.25 hPa). The sublimation temperature may be the normal sublimation temperature, i.e. the sublimation temperature at normal pressure (1013.25 hPa). The chamber comprises at least one opening via which the indicator substance can escape from the inner space of the chamber in the case of the exceeding of its boiling point or its sublimation point. The at least one opening or the chamber is arranged so that the indicator substance in the liquid or solid state cannot escape out of the chamber via the opening. The opening may be formed, for example, via a capillary, for example, a bent capillary via which the inner space is fluidically connected to the surroundings. The device may also comprise several such chambers.

As a result of the chamber according to the invention, an additional compartment is thus provided which is filled with a liquid or a solid body, which possesses in the case of a threshold temperature between −140° C. and −10° C. its boiling or sublimation point, as the indicator substance. The indicator substance can only escape via the at least one opening of the chamber in the gaseous state, i.e. the fill level in the chamber which serves as a test volume reduces as a result of the boiling or sublimation of the indicator substance. If a threshold temperature to be monitored which corresponds to the boiling temperature or the sublimation temperature of the indicator substance is exceeded, the indicator substance becomes gaseous and can escape from the inner space of the chamber via the at least one opening. If it is thus determined at a subsequent check time that the quantity of solid or liquid indicator substance in the chamber has reduced, it can be concluded that the threshold temperature was exceeded in the interim, at least briefly. The chamber can therefore be used as an indicator element or indicator apparatus in order to display an undesirable exceeding of the threshold temperature.

One particular advantage of the device according to the invention is furthermore that a measure for the duration of a past exceeding of the boiling temperature or the sublimation temperature can be derived from the quantity of indicator substance which is still located in the chamber at a specific point in time. Although the quantity of the reduction is not only dependent on the duration, but also on the level of the exceeding of the temperature, it nevertheless provides an indication of whether the case involves a brief exceeding which may potentially be tolerable or a longer period of time.

By way of example, the following substances may be stated which can be used as the indicator substance and can be discharged into the surrounding atmosphere in small quantities without any problems: nitrous oxide ($N_2O$) (boiling point: −88.46° C., melting point: −90.86° C.), dry ice ($CO_2$) (sublimation point: −78.50° C.) or ammonia ($NH_3$) (boiling point: −33.35° C., melting point: −77.72° C.). A series of further compounds with suitable boiling points or sublimation points which are also suitable for the stated purpose may be inferred from relevant chemical tables. A substance, the boiling point or sublimation point of which corresponds to or at least comes close to a predetermined threshold temperature, the exceeding of which should be monitored, may thus expediently be selected as the indicator substance.

For the purpose of improved detectability, the indicator substance may comprise an indicator additive which improves detectability of a physical property of the indicator substance. The indicator additive may be, for example, a dye so that the indicator substance is colored or dyed, i.e. not transparent. The quantity of indicator substance which is still located in the chamber at a check time can then be determined more easily. The indicator additive may be particles, in particular nanoparticles which increase a scattering action and/or polarization action of the indicator substance for electromagnetic radiation striking the indicator substance. As a result, a quantity of indicator substance which is still located in the chamber at a check time may be detected more reliably by means of optical transmission measurement, scattering measurement and/or polarization measurement. The indicator additive may be conductive particles. The conductivity or impedance of the indicator substance may be influenced by adding conductive particles. In this manner, a change in configuration of the indicator substance can be detected by means of a conductivity measurement or impedance measurement. As a result of the added indicator additive, the corresponding property of the indicator substance can be detected with a correspondingly, expediently formed measuring apparatus in order to be able to determine a fill level of the indicator substance in the chamber more reliably.

According to a further preferred embodiment, the device may have a plurality of chambers which are filled in each case at least partially with an indicator substance, the boiling temperature or sublimation temperature of which lies in a range from −10° C. to −140° C., wherein the indicator substances in the chambers have different boiling temperatures or sublimation temperatures.

For example, a container for the formation of several chambers may have several sub-cavities formed by dividing walls. In this case, each sub-cavity forms a chamber which contains one of the indicator substances. The indicator substances in the chambers can have different boiling or sublimation temperatures. Different temperature threshold values can thus be monitored, wherein each indicator substance is selected so that its boiling temperature or sublimation temperature corresponds to or at least comes close to one of the temperature threshold values to be monitored. This embodiment has the advantage that the achieved temperature intervals which the sample reaches can be restricted more precisely.

Moreover, a wall of the at least one chamber may be embodied to be transparent or semi-transparent at at least one point so that the fill level of the chamber can be observed from the outside.

It is furthermore advantageous if a wall of the at least one chamber comprises a scale to display a fill level of the indicator substance in the inner space and/or a scale to display a duration of the exceeding of the boiling point or the sublimation point of the indicator substance. The relationship between fill level of the chamber and duration of the exceeding of the boiling point or the sublimation point can, for example, be checked experimentally in advance. This variant is particularly suitable for visual inspection.

According to a further aspect of the invention, the device may comprise a measuring apparatus which is formed to determine a fill level of the indicator substance in the inner space of the at least one chamber. This variant is particularly suitable for automated temperature monitoring of cryogenic samples. The measuring apparatus may, merely by way of example, be an optical or optical-electric measuring apparatus in order to determine the fill level of the indicator substance e.g. with an optical transmission, scattered light or reflection measurement.

According to one preferred embodiment, a material with a liquid-absorbing structure, for example, a porous material, may be present in a sub-region of the chamber into which the at least one opening does not discharge.

This embodiment is advantageous in the case of an indicator substance which does not sublimate directly, but rather is liquid in a temperature range below its boiling point, e.g. nitrous oxide. In the liquid state, the indicator substance can then diffuse slowly into the material with a liquid-absorbing structure, which can be read quantitatively. If the storage temperature is above the boiling temperature, the nitrous oxide evaporates via the at least one opening of the chamber. The reduction in the level of the indicator substance is then the measure for the exceeding of the threshold temperature to be monitored and the porous material is also free from it. Much more information about the storage temperature can be obtained from this combination finding than by way of pure melting of a substance. Moreover, the loss of the material is tamper-proof in the case of a particular composition. Refilling can also be prevented in a suitable manner.

The at least one chamber may be formed by a container with one or more cavities which can be arranged and/or is arranged on the outside of the sample container. The term "can be arranged and/or is arranged" should encompass "can be fastened and/or is fastened", "can be coupled and/or is coupled", "can be connected and/or is connected". The container for the formation of the at least one chamber which is at least partially filled with indicator substance should thus be differentiated from the sample container.

In this case, the container can be capable of being arranged and/or be arranged on the outside of the container or inside the container. One possibility of the realization according to the invention provides that the container for the formation of the at least one chamber is fastened detachably to the sample container. A detachable fastening should in particular also encompass sliding or pushing the container onto the sample container. This has the advantage that the container can be stored and prepared (e.g. filling with the indicator substance) spatially separate from the sample container.

For example, the sample container may comprise a cover for closing off the receiving space. According to one preferred exemplary embodiment, the at least one chamber may be integrated into the cover, e.g. into the head part and/or the shaft of the cover. For example, the cover may comprise a shaft which is in engagement with an upper end region of the receiving space of the sample container, wherein the at least one chamber is integrated into the shaft. According to one preferred variant of this exemplary embodiment, the sample container is a cryogenic tube, comprising a cover for closing off the receiving space which has a shaft which is in engagement with an upper end region of the receiving space. In this case, the at least one chamber is integrated into the shaft, and a head part of the cover sitting on the shaft comprises, for the formation of the at least one opening, a passage opening which connects the inner space of the chamber to the surroundings.

The arrangement of the at least one chamber in the cover has the particular advantage that no additional installation space is required outside the sample container. A further advantage is that the at least one chamber which serves as an indicator apparatus can be stored and prepared (e.g. filling the chamber with the indicator substance and cooling the indicator substance so that it becomes solid or liquid) together with the cover spatially separate from the rest of the sample container.

A further possibility of the realization according to the invention provides that the at least one chamber is formed by a container and that there is provided on an outer wall of the sample container a receptacle, for example, a sleeve or insertion pocket into which the container can be inserted and/or is inserted for retention on the sample container.

According to a further advantageous embodiment, the at least one chamber may be formed by a double-walled push-on part which can be pushed or slid onto an outer shell surface of the sample container and at least partially engages around it in the pushed-on state. This variant is particularly advantageous for cylindrical sample containers, in particular cryogenic tubes. The double-walled push-on part may be embodied as a hollow cylinder or partial hollow cylinder, the inner diameter of which corresponds to the outer diameter of the sample container so that the push-on part engages around the cylindrical sample container in the manner of a cuff or clamp.

The sample container may furthermore be glued, melted or fixed in another manner to the push-on part. As a result, a removal of the push-on part for manipulation purposes, e.g. to replace a push-on part which exhibits undesirable heating with a new push-on part, can be prevented.

The term sample container refers preferably to a container which is configured for cryopreservation, for example, a tube, a straw (also referred to as a seed tube), a bag for blood or stem cell storage, a box or another container which is suitable for cryopreservation. Such containers are correspondingly also referred to as cryogenic tubes, cryogenic straws, cryogenic bags, cryogenic boxes or generally as cryogenic containers.

Cryogenic tubes are also referred to as biobank or cryobank tubes. Cryogenic tubes have a receiving space which forms an inner cavity for receiving a biological sample. The cryogenic tube furthermore normally has a cover for closing off the receiving space. The cover may comprise an engagement via which the cover can be rotated with a tool. The cryogenic tube may also comprise a base element which has a marking, e.g. in the form of machine-readable code.

The sample container is preferably produced using low-temperature-compatible plastic material for temperatures below −140° C. The plastic material can tolerate repeated temperature changes without change and without damage. A plastic material is preferably used, the water absorbing capacity of which is <1% of the net mass, in particular <0.1% of the net mass. Cryogenic storage elements according to the invention are based, for example, on polyurethane or polyethylene.

The term "biological sample" refers to biological material such as cells, tissue, cell components, biological macromolecules, etc. which are subjected to cryopreservation in the sample container, where applicable, in a suspension and/or in combination with a substrate material. A substrate which is configured for adherent receiving of biological cells which are part of the biological sample can thus be arranged in the receiving space.

According to a second aspect of the invention, the stated objects are achieved by a method for temperature monitoring of cryopreserved samples which uses a device for temperature monitoring, as described in this document. The embodiments relating to the device, in particular their advantageous embodiment variants, should thus also be regarded as disclosed according to the method and be capable of being claimed in order to avoid repetition.

A substance, the boiling or sublimation temperature of which corresponds to or at least comes close to a predetermined threshold temperature, the exceeding of which should be monitored, may preferably be selected as the indicator substance.

According to the method, a device for temperature monitoring, as described in this document, may thus be provided, wherein the device contains at least one indicator substance in the liquid or solid state in the at least one chamber, wherein the boiling temperature or sublimation temperature of the indicator substance lies in a range from −10° C. to −140° C. The chamber comprises at least one opening via which the indicator substance can escape from the inner space of the chamber in the case of the exceeding of its boiling point or sublimation point. The receiving space of the sample container preferably contains a cryopreserved biological sample.

The method further comprises cooled storing of the device for cryopreservation. The method further comprises monitoring of the fill level of the at least one indicator substance in the at least one chamber.

If the fill level has reduced after the start of cryogenic storage in comparison with the starting fill level, indicator substance must have escaped in gaseous form from the at least one opening. Consequently an exceeding of the boiling or sublimation temperature and thus of the threshold temperature to be monitored can be concluded, in particular when the exceeding has only occurred for a brief period of time.

One particular advantage of the invention thus lies in the fact that the current fill level of the indicator substance in the chamber directly shows whether a cryogenic sample has heated up above a definable threshold temperature, even if only briefly. This can be quickly and easily determined by visual inspection or also in a technically automated manner by means of a correspondingly configured measuring apparatus without the sample having to be removed from the sample container or thawed out.

According to one advantageous further development of the method, a parameter may furthermore be determined which indicates a change in the quantity of indicator substance in the respective chamber and/or which indicates a measure for the period of time which the sample has spent at a temperature above the boiling point or the sublimation point of the indicator substance.

BRIEF DESCRIPTION OF THE DRAWINGS

The preferred embodiments and features of the invention described above may be combined with one another. Further details and advantages of the invention are described below with reference to the enclosed drawings. In the drawings.

DETAILED DESCRIPTION OF PREFERRED EMBODIMENTS

Identical elements or functionally equivalent elements are designated by the same reference numbers in all the figures and are partially not described separately.

FIG. 1A shows by way of example an open cryogenic tube 1 in a sectional view, representative of other cryogenic sample containers, such as straws, bags, boxes etc. Such cryogenic tubes 1 are also referred to as biobank tubes.

Cryogenic tube 1 generally comprises a receiving volume 2 for the biosample in which the biomaterials are located. The biosample here is a cell suspension 6. The cryogenic tube is shown in FIG. 1A still without a screw cover closure. The cryogenic tube further comprises a cover (screw cover closure) 3 shown in FIG. 1B which closes off cryogenic tube 1 and at the top has an engagement 4 via which cover 3 can be turned with a tool (not shown) in the case of automation. These cryogenic tubes 1 can also contain a base into which a barcode square or another mark is optionally inserted. In this form, usually standing perpendicular in receptacles, cryogenic tubes 1 are stored in the low-temperature containers.

Storage-ready device 10 for cryogenic storage is represented in FIG. 1B. Cover 3 has a head part 9 which sits on receiving volume 2 and a shaft 5 formed thereon which engages into receiving volume 2 in the screwed state. The corresponding region of receiving volume 2 has a thread 8. A chamber 11 which forms a test volume is integrated into screw cover 3.

Chamber 11 has one or more open connections 13 to the outer space and has no connection to receiving space 2 of the cryogenic tube in which biosample 6 is located.

Chamber 11 is cooled separately and filled with indicator substance 7. This can be carried e.g. by the throughflow of $CO_2$ gas or nitrous oxide which becomes liquid or solid in chamber 11 as a result of the low temperature (<−140° C.). If volume 12 of chamber 11 is partially or fully filled, cryogenic tube 1 is closed off with cover 3, as shown in FIG. 1B. The filling of indicator substance 7 is represented by the black area.

If sample 6 is stored in an unauthorized manner at a temperature above −78.5° C. in the case of dry ice as indicator substance 7, the solid $CO_2$ sublimates and escapes via opening 13 into the surroundings which is represented by reference number 14. As a result, over time, the fill level of the filling reduces by difference Δx. Both the breach of the threshold temperature and to a certain extent the period of incorrect storage can be determined on the basis of the level of the chamber filling. This is represented in FIG. 1C. To this end, the test substance can also be dyed in a suitable manner or determined in terms of their quantity via sensors.

Device 10, formed from sample container 1 and integrated chamber 11 which is filled with indicator substance 7, is thus configured for temperature monitoring of a cryopreserved biological sample.

According to a further variant which is represented in FIG. 1D, the inner space of chamber 11 can also be filled partially at the bottom with a porous material 15 into which a liquid diffuses slowly. If e.g. instead of $CO_2$, nitrous oxide ($N_2O$) as indicator substance 7 is conducted through the cold volume of chamber 11, the space fills above the porous material, as shown in FIG. 1D, with indicator substance 7 and becomes solid at a temperature of <−140° C. If device 10 is thus later heated in the perpendicular position above melting temperature −90.86° C. and stored for a longer period of time, the liquid nitrous oxide diffuses into the porous material, which can be quantitatively read. If the storage temperature lies above −88.46° C., the nitrous oxide evaporates via openings 13a into the surroundings. The reduction in the nitrous oxide level is then the measure and the porous material is also free of this. Much more information about the storage temperature can be obtained from this combination finding than by way of pure melting of a substance. Moreover, the loss of the material is tamper-proof in the case of a particular composition. Refilling can also be prevented in a suitable manner.

Figure 2:
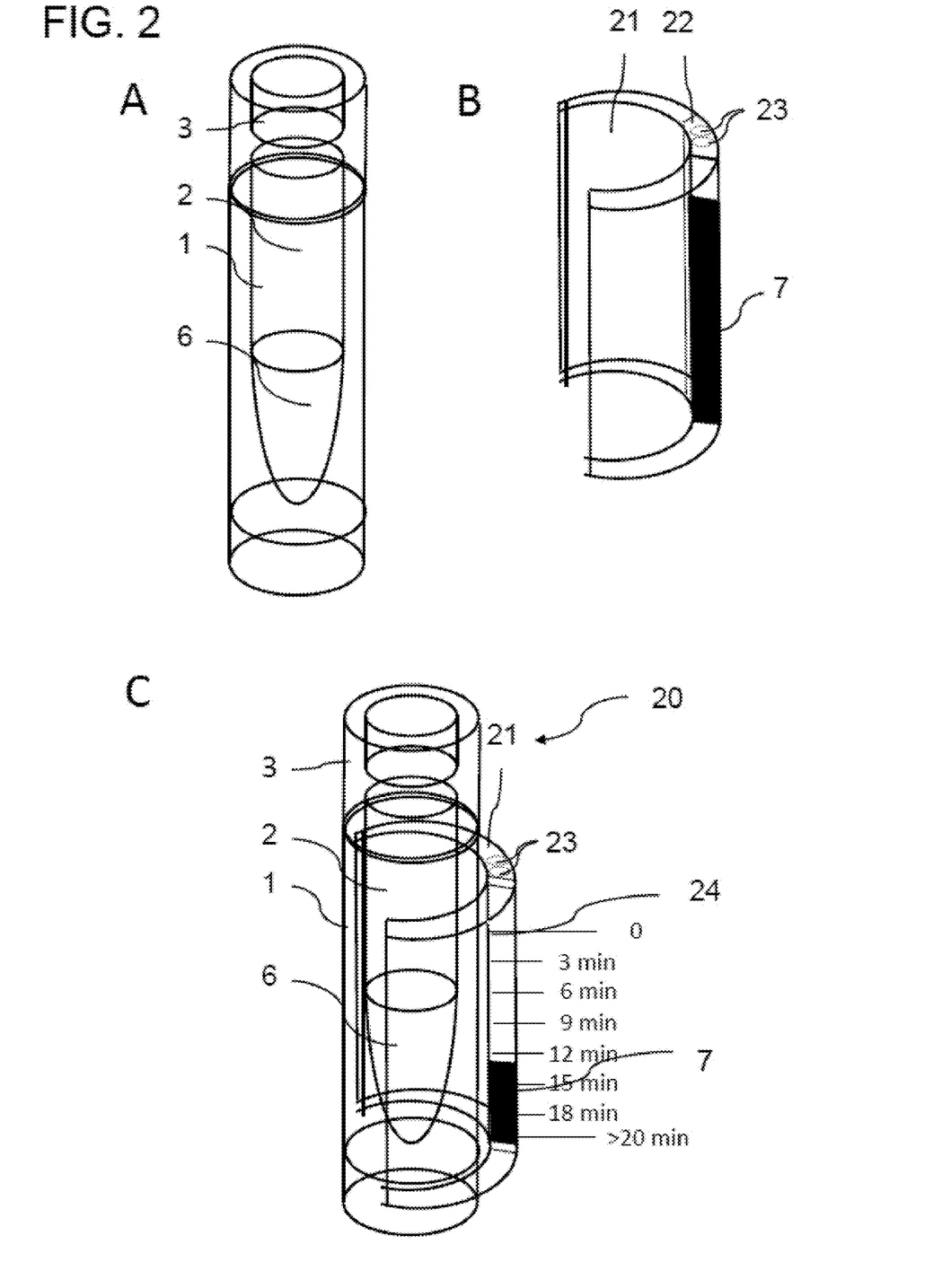
FIG. 2 show schematic views of a second exemplary embodiment of a device for temperature monitoring of a cryopreserved biological sample.

FIG. 2A initially shows a cryogenic tube 1 which is fully closed with a cover 3, as is normally used in cryobanks. FIG. 2B shows a push-on part 21 which is embodied to be double-walled, which is composed of plastic and which can be placed on the outer shell surface of cryogenic tube 1, as represented in FIG. 2C.

Figure 1:
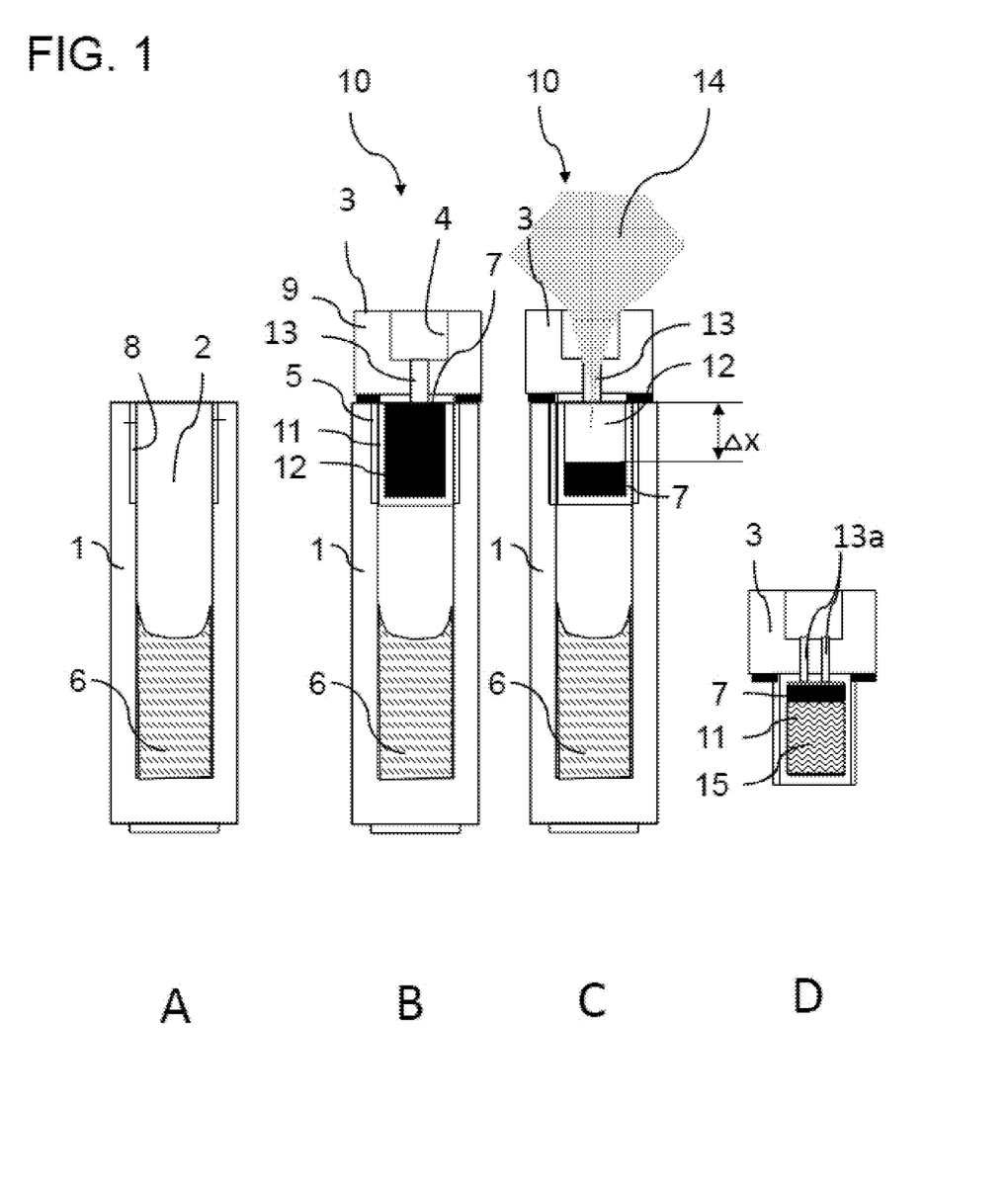
FIGS. 1A-1C show schematic views of a first exemplary embodiment of a device for temperature monitoring of a cryopreserved biological sample.
FIG. 1D shows a schematic view of one variant of the first exemplary embodiment.

A volume 22 which is filled with an indicator substance 7 is located in this plastic part 21 in an analogous manner to the exemplary embodiment illustrated in FIG. 1 in a perpendicular alignment. The volume has two openings 23 via which a gas (e.g. $CO_2$ gas or nitrous oxide) or a liquid can be introduced.

This additional part 21 can be pushed onto and clamped on existing cryogenic tubes 1, as shown in FIG. 1C. This is carried out at the storage temperature, generally below $-140°$ C., so that indicator substance 7 in push-on part 21 is liquid or solid and cannot escape via openings 23.

In an analogous manner to the exemplary embodiment illustrated in FIG. 1, indicator substance 7 only then escapes from inner space 22 via openings 23 when a boiling or sublimation temperature of indicator substance 7 was exceeded and indicator substance 7 undergoes a transition into the gaseous state.

FIG. 2C shows a state in which indicator substance 7 has already largely escaped from inner space 22.

The wall of the push-on part has a scale 24 and is embodied transparently at this point so that the fill level of indicator substance 7 can be seen from the outside. The reduction in indicator substance 7 can also be detected over time via scale 24. In an analogous manner, such systems can also be fastened to boxes, cases, straws and bags or other conventional cryogenic containers.

Figure 3:
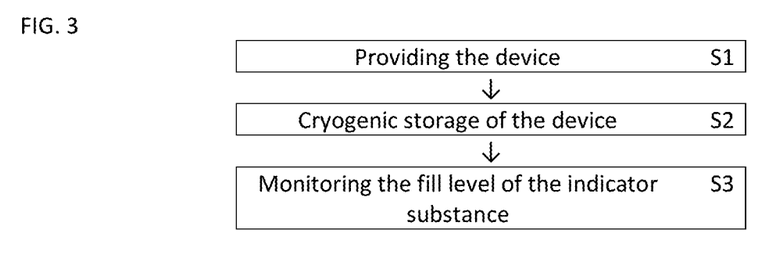
FIG. 3 shows a flow chart to illustrate an exemplary embodiment of a method for temperature monitoring of a cryopreserved biological sample.

FIG. 3 illustrates on the basis of a flow chart a method for temperature monitoring of a cryopreserved biological sample. In step S1, a device according to the invention for temperature monitoring is provided, for example, one of devices 10 or 20, the chamber of which is filled with the indicator substance. In this case, a substance which has a suitable boiling point or sublimation point is to be selected as indicator substance 7 depending on the temperature threshold value which should be monitored during cryogenic storage.

In step S2, the device with a cryogenic sample is stored in the receiving space of the sample container at a storage temperature below the boiling temperature or the sublimation temperature of the indicator substance.

It is subsequently possible to check by means of the indicator substance at any desired point in time during the storage process whether an undesirable, if only temporary heating of the cryosample has taken place (step S3). To this end, in each case the fill level of the chamber is checked, i.e. whether and possibly to what extent the fill level of indicator substance has changed in comparison with an initial state. If it is ascertained at a later check time that the quantity of solid or liquid indicator substance in the chamber has reduced, it can be concluded that the threshold temperature was exceeded in the interim, at least briefly. The chamber can therefore be used as an indicator element or indicator apparatus in order to display an undesirable exceeding of the threshold temperature.

Although the invention has been described with reference to specific exemplary embodiments, it is apparent for a person skilled in the art that various changes can be made and equivalents can be used as a replacement without departing from the scope of the invention. The invention should consequently not be restricted to the disclosed exemplary embodiments, but rather should enclose all the exemplary embodiments which fall into the scope of the enclosed claims. In particular, the invention also claims protection for the subject matter and the features of the subordinate claims independently of the claims referred to.

The invention claimed is:

1. A device for temperature monitoring of a cryopreserved biological sample, comprising
    a) a sample container with a receiving space for receiving a biological sample; and
    b) at least one chamber, an inner space of which is not fluidically connected to the receiving space and is at least partially filled with an indicator substance, a boiling temperature or a sublimation temperature of which lies in a range from $-10°$ C. to $-140°$ C., wherein the at least one chamber comprises at least one opening via which the indicator substance can escape from the inner space of the chamber in a case of exceeding of the boiling temperature or the sublimation temperature of the indicator substance.

2. The device according to claim 1, wherein there is a plurality of chambers at least partially filled with indicator substances, the boiling temperature or the sublimation temperature of which lies in a range from $-10°$ C. to $-140°$ C., wherein the indicator substances in the chambers have different boiling temperatures or sublimation temperatures.

3. The device according to claim 1, wherein a wall of the at least one chamber is transparent or semi-transparent at at least one point.

4. The device according to claim 1, wherein a wall of the at least one chamber comprises a scale to display a fill level of the indicator substance in the inner space and/or a scale to display a duration of the exceeding of the boiling temperature or the sublimation temperature of the indicator substance.

5. The device according to claim 1, further comprising a measuring apparatus which is configured to determine a fill level of the indicator substance in the inner space of the at least one chamber.

6. The device according to claim 1, wherein the indicator substance
    a) is nitrous oxide ($N_2O$), dry ice ($CO_2$) or ammonia ($NH_3$); and/or
    b) is colored.

7. The device according to claim 1, wherein the opening is formed by a capillary via which the inner space is fluidically connected to surroundings of the device.

8. The device according to claim 1, wherein a material with a liquid-absorbing structure is present in a sub-region of the chamber into which the opening does not discharge.

9. The device according to claim 1, wherein the at least one chamber is arranged in an interior of the sample container.

10. The device according to claim 1, wherein
    a) the sample container is a cryogenic tube, having a cover for closing off the receiving space which has a shaft which is in engagement with an upper end region of the receiving space,
    b) the at least one chamber is integrated into the shaft; and
    c) a head part, which sits on the shaft of the cover has a passage opening for forming the at least one opening.

11. The device according to claim 1, wherein the at least one chamber is formed by a container which can be arranged and/or is arranged on an outside of the sample container.

12. The device according to claim 1, wherein the at least one chamber is formed by a container which can be pushed onto an outer shell surface of the sample container and at least partially engages around the outer shell surface of the sample container in the pushed-on state.

13. A method for temperature monitoring of cryopreserved samples, comprising the steps:
   a) providing a device for temperature monitoring according to claim 1, which contains at least one indicator substance in a frozen state in the at least one chamber, wherein the receiving space contains a cryopreserved sample;
   b) cooled storing of the device for cryopreservation; and
   c) monitoring a fill level of the at least one indicator substance in the at least one chamber.

14. The method according to 13, wherein a parameter is determined which indicates a change in a quantity of indicator substance in the respective chamber and/or which indicates a measure for a period of time which the sample has spent at a temperature above the boiling temperature or the sublimation temperature of the indicator substance.

15. The method according to claim 13, wherein a substance is selected as the indicator substance, the boiling temperature or the sublimation temperature of which corresponds to a predetermined threshold temperature, an exceeding of which is monitored.

\* \* \* \* \*